(12) United States Patent
Kreindel et al.

(10) Patent No.: US 8,084,377 B2
(45) Date of Patent: *Dec. 27, 2011

(54) PROTECTIVE MATERIAL, CLOTHING ITEM AND METHOD OF PROTECTION

(75) Inventors: Michael Kreindel, Richmond Hill (CA); Mark Gray, Herne Bay (NZ); Christopher Hawthorne, Brookfield (AU)

(73) Assignee: Sun-Soul Inc. (CA)

( * ) Notice: Subject to any disclaimer, the term of this patent is extended or adjusted under 35 U.S.C. 154(b) by 445 days.

This patent is subject to a terminal disclaimer.

(21) Appl. No.: 12/008,410

(22) Filed: Jan. 10, 2008

(65) Prior Publication Data

US 2008/0179573 A1 Jul. 31, 2008

Related U.S. Application Data (63) Continuation of application No. PCT/AU2006/000991, filed on Jul. 14, 2006.

(51) Int. Cl.
*B32B 27/04* (2006.01)
*C09B 67/00* (2006.01)

(52) U.S. Cl. ............... 442/133; 442/131; 8/922; 8/926; 8/928; 8/637.1; 8/648

(58) Field of Classification Search .............. 442/131, 442/133; 8/637.1, 648
See application file for complete search history.

(56) References Cited

U.S. PATENT DOCUMENTS

| | | | |
|---|---|---|---|
| 2,391,959 A | 1/1946 | Gallowhur | |
| 3,467,482 A * | 9/1969 | Maerov | ............... 8/512 |
| 5,007,109 A | 4/1991 | Wheeler | |
| 5,066,082 A | 11/1991 | Longstaff | |
| 5,414,913 A | 5/1995 | Hughes | |
| 5,503,917 A | 4/1996 | Hughes | |
| 5,515,542 A * | 5/1996 | Simmons | ............... 2/67 |
| 5,544,361 A | 8/1996 | Fine et al. | |
| 6,017,360 A | 1/2000 | Chubb et al. | |
| 6,034,003 A | 3/2000 | Lee | |
| 6,037,280 A | 3/2000 | Edwards et al. | |
| 6,194,330 B1 | 2/2001 | Vogt et al. | |
| 6,350,168 B1 | 2/2002 | Kroll et al. | |
| 6,482,757 B2 | 11/2002 | Vogt et al. | |
| 6,645,230 B2 | 11/2003 | Whitehurst | |
| 6,676,655 B2 | 1/2004 | McDaniel | |
| 6,835,202 B2 | 12/2004 | Harth et al. | |
| 6,968,574 B2 | 11/2005 | Kroll | |
| 7,289,205 B2 | 10/2007 | Yaroslavsky et al. | |
| 2002/0157165 A1 * | 10/2002 | Kroll et al. | ............... 2/69 |
| 2003/0004556 A1 | 1/2003 | McDaniel | |

(Continued)

FOREIGN PATENT DOCUMENTS

DE 3141692 A1 5/1983

(Continued)

OTHER PUBLICATIONS

Printout from website www.cooltan.com, 2 pages, (2006).
Int'l Search Report for PCT/AU2006/000911, dated Aug. 4, 2006.

*Primary Examiner* — Lynda Salvatore
(74) *Attorney, Agent, or Firm* — Harness, Dickey & Pierce, P.L.C.

(57) ABSTRACT

A material and method delivering to the skin therapeutic radiation and filtering a part of the sun spectrum causing skin damage.

38 Claims, 7 Drawing Sheets

U.S. PATENT DOCUMENTS

| | | |
|---|---|---|
| 2003/0009158 A1 | 1/2003 | Perricone |
| 2003/0060719 A1 | 3/2003 | Irion et al. |
| 2003/0127633 A1 | 7/2003 | Heidenfelder et al. |
| 2006/0236470 A1 * | 10/2006 | Sabnis et al. .................. 8/405 |

FOREIGN PATENT DOCUMENTS

| | | |
|---|---|---|
| EP | 0267655 B1 | 9/1992 |
| GB | 2 161 508 A | 1/1986 |
| WO | WO 98/51172 | 11/1998 |
| WO | WO 2004/090589 | 10/2004 |

* cited by examiner

Undyed shirt material
84/16 nylon/spandex

Fig. 5B

Shirt material dyed with fluorescent dye
Density = 99% (SPF>50)

Fig. 6A

Undyed hat material
65/35 polyester/cotton

Fig. 6B

Hat material with fluorescent dye
Density = 99% (SPF>50)

Fig. 5C

PROTECTIVE MATERIAL, CLOTHING ITEM AND METHOD OF PROTECTION

CROSS REFERENCE TO RELATED APPLICATIONS

This application is a continuation of International Application PCT/AU2006/000991 filed Jul. 14, 2006 that claims priority to U.S. application Ser. No. 11/181,346 filed Jul. 14, 2005, all of which are hereby incorporated by reference.

FIELD OF THE INVENTION

This invention relates to a protective material, a clothing item and methods of protection and therapy and especially, but not exclusively, to use of special materials for manufacturing clothes which can effectively convert incident radiation in the form of sunlight to light comprising substantially wavelengths having dermatological therapeutic effect and in which wavelengths having deleterious effect are reduced, compared to sunlight.

BACKGROUND OF THE INVENTION

Various light sources have been proposed for therapy of different dermatological problems. For example, blue light in the range of 400-420 nm or 400-450 nm or has been found helpful for acne treatment. U.S. Pat. No. 6,835,202 describes a device for acne treatment having spectrum 405-440 nm. Red light at 590 nm and 632 nm is used for skin rejuvenation and U.S. Pat. No. 6,676,655 describes a method of skin treatment using devices emitting light in narrowband multichromatic spectrum having the wavelengths corresponding to tissue absorption peaks. U.S. Pat. No. 6,645,230 describes devices for photodynamic therapy using specific light spectrum ranges.

Although some wavelengths of the electromagnetic spectrum have strong therapeutic effect, the full broad spectrum of sunlight, (which includes ultraviolet, visible and infrared ranges) is known to have deleterious effects on the skin. For example, exposure to direct sunlight is a major reason for skin damage and premature aging, and (particularly the ultraviolet component) can cause skin cancer.

SUMMARY OF THE INVENTION

According to a first aspect of the present invention there is provided a material having the following optical properties:
absorption of at least a substantial proportion of the electromagnetic radiation in sunlight that causes skin damage; and
transmission of a substantial amount of electromagnetic radiation in sunlight that has therapeutic effect for the human skin.

According to a second aspect of the present invention there is provided a material having the following optical properties:
absorption of at least a substantial proportion of the electromagnetic radiation in sunlight that causes skin damage; and
converting at least part of the absorbed radiation to radiation having therapeutic effect on human skin.

According to a third aspect of the present invention there is provided a material having the following optical properties:
absorption of at least a substantial proportion of the electromagnetic radiation in sunlight that causes skin damage;
transmission of at least a part of the electromagnetic radiation in sunlight that has a therapeutic effect on human skin; and
converting at least part of the absorbed radiation to radiation that has a therapeutic effect on human skin.

Preferably, the optical properties of the material are at least partially resultant from the material having been dyed with one or more pigments. Such a material could be in the form of a continuous non-porous sheet of material.

Preferably, the said material is a fabric. Providing the material as a fabric facilitates making clothes out of the material, which allow convenient protection from sunlight simultaneous with delivery of therapeutic radiation to the wearer. An umbrella, parasol or sun shade incorporating the material could provide similar benefits, but would often be less convenient in use.

Preferably, said fabric is made from polymer fiber, although other fibres or combinations of fibres could be used.

The fabric may comprise a spandex (elastane) component.

The fiber may be dyed with one or more pigments.

One or more pigments may be a fluorescent agent. Reference to a dying a fiber with a pigment should be construed as including any technique for imparting pigmentation or fluorescent agents to a fiber, whether individually or when the fibre is part of a material or fabric. The fibre may be dyed using a fluorescent agent, and many such agents are commercially available, including many which are marketed for and/or previously used in pumped dye lasers. The dye may be imbedded in a polymer fibre or, as one (but not the only) alternative a more conventional immersion-type dying process can be used.

Said radiation that has a therapeutic effect on human skin can include wavelengths absorbed by porphyrin.

Said radiation that has a therapeutic effect on human skin preferably has wavelengths greater than about 400 nm.

Said radiation that has a therapeutic effect on human skin can include wavelengths in the range of 400-490 nm.

Said radiation that has a therapeutic effect on human skin can include wavelengths stimulating collagen growth.

Said radiation that has a therapeutic effect on human skin can include wavelengths from 590 nm to 670 nm.

Said radiation that has a therapeutic effect on human skin can include wavelengths stimulating tissue healing.

Said radiation that has a therapeutic effect on human skin can include wavelengths from 700 nm to 900 nm.

Some embodiments comprise two different fluorescent dyes, a first of which fluoresces at a first therapeutic wavelength and a second of which fluoresces at a second distinct wavelength. In one embodiment a first dye fluoresces radiation which includes wavelengths in the range of 400-490 nm, and a second dye fluoresces radiation which includes wavelengths in the range of 700-900 nm.

It will be appreciated that none of the above wavelength ranges should be construed as indicating that the material necessarily transmits or emits or fluoresces at all wavelengths in the stated range, or across the entire breadth of the stated range.

Preferably at least some of said radiation that causes skin damage has a wavelength less than about 400 mm.

Preferably at least some of the electromagnetic radiation in sunlight that causes skin damage which is absorbed by the material is ultra-violet radiation.

Preferably, the material prevents transmission therethrough of at least 50% of said radiation that causes damage in human skin.

Preferably the material prevents transmission therethrough of at least 75% of said radiation that causes damage in human skin.

Preferably the material prevents transmission therethrough of at least 90% of said radiation that causes damage in human skin.

Preferably the material prevents transmission therethrough of at least 98% of said radiation that causes damage in human skin.

In some embodiments it is preferable that the material allows transmission therethrough of at least 50% of a specific wavelength or selection of wavelengths of radiation in sunlight that have a therapeutic effect on human skin.

In some embodiments it is preferable that the material allows transmission of at least 70% of the said one or more selected therapeutic wavelengths.

In some embodiments it is preferable that the material allows transmission of at least 90% of the said one or more selected therapeutic wavelengths.

It will be appreciated that the above percentages relate to percentages of incident radiation (of the type specified), under normal conditions, with the angle of incidence of the radiation to the material being approximately 90 degrees.

In embodiments which include the property of converting absorbed radiation to radiation that has a therapeutic effect on human skin the amount of radiation of a given therapeutic wavelength may exceed the amount of radiation of that wavelength provided by the sunlight incident on the material.

The material may comprise a first layer and a second layer with different optical properties.

The first layer may include a fluorescent agent for emitting therapeutic radiation.

The second layer may have a filtration function to filter out a substantial amount of radiation that causes skin damage.

In preferred embodiments the optical properties of the material are such that when the material is provided between the skin of a user and the sun and exposed to sunlight, an amount of therapeutic radiation adequate to have a substantial effect on a condition to be treated, can be delivered to the skin from the material.

In the case of use of the material in an umbrella or parasol or sunshade the distance between the material and the skin will normally be from a few centimetres to a few metres.

In the case of an item of clothing the material will normally be close to the skin.

Typically the optical properties of the material will be such that the amount of therapeutic radiation in a desired spectral band, adequate to have a substantial effect on a condition to be treated can be delivered to the skin and so that the delivered intensity of radiation at certain (and preferably most) wavelengths in spectral bands close to and on either side of the desired spectral bands, will be considerably less than the delivered intensity of at least some of the wavelengths in the desired spectral band.

In some preferred embodiments the optical properties of the material are such that the in use, the material delivers effective amounts of therapeutic radiation wavelengths in a desired spectral band (400 nm to 500 nm in one embodiment) at intensities several times greater than the delivered intensities of shorter wavelengths (between 400 nm and 380 nm, or shorter, in said one embodiment) and at intensities at least twice the delivered intensities of many longer wavelengths (between about 500 nm and 700 nm in said one embodiment).

According to a fourth aspect of the present invention there is provided a portable item which includes at least portion made from a material having optical properties such that in use, when being carried or worn by a wearer in sunlight, the said material can protect at least an area of the wearer's skin from electromagnetic radiation in sunlight that causes skin damage, while allowing radiation that has a therapeutic effect on human skin to be transmitted from the said material to said area of the wearer's skin.

The item can be an item of clothing.

The item of clothing may be a shirt or a hat or some other clothing item.

The material is preferably in accordance with at least one of the first, second and third aspects.

The portable item preferably comprises an item of clothing comprising fabric which includes a fluorescent component which emits at one or more wavelengths in a selected spectral band which has a therapeutic effect, such that emitted therapeutic radiation can be delivered to the skin of a wearer of the item, and such that when the item is worn in sunlight sufficient radiation within the selected spectral band is delivered to the skin to have a therapeutic effect. (The therapeutic radiation delivered to the skin may be a combination of radiation by the fluorescent agent and components of sunlight transmitted by the fabric.)

According to a fifth aspect of the present invention there is provided a method for protection of the skin from electromagnetic radiation in sunlight that causes skin damage, comprising:

delivering some of the electromagnetic radiation from sunlight to the skin, through a material having the following optical properties:

absorption of at least a substantial proportion of the electromagnetic radiation in sunlight that causes skin damage; and transmission of a substantial amount of electromagnetic radiation in sunlight that has therapeutic effect for the human skin;

and thereby allowing exposure of the skin to electromagnetic radiation from sunlight that has therapeutic effect for human skin.

According to a sixth aspect of the present invention there is provided a method for protection of the skin from electromagnetic radiation in sunlight that causes skin damage, comprising:

preventing delivery of at least some of the electromagnetic radiation in sunlight to the skin, by providing a barrier to sunlight, said barrier being at least partially formed by a material having the following optical properties:

absorption of at least a substantial proportion of the electromagnetic radiation in sunlight that causes skin damage;

converting at least part of the absorbed radiation to radiation having therapeutic effect on human skin;

and thereby allowing exposure of the skin to electromagnetic radiation that has therapeutic effect for human skin.

According to a seventh aspect of the present invention there is provided a method for protection of the skin from electromagnetic radiation in sunlight that causes skin damage, comprising:

delivering some of the electromagnetic radiation from sunlight to the skin, through a material having the following optical properties:

absorption of at least a substantial proportion of the electromagnetic radiation in sunlight that causes skin damage; and transmission of a substantial amount of electromagnetic radiation in sunlight that has therapeutic effect for the human skin;

converting at least part of the absorbed radiation to radiation having therapeutic effect on human skin;

and thereby allowing exposure of the skin to electromagnetic radiation that has a therapeutic effect for human skin.

The method may be used for skin therapy.

A topical agent can be applied to the skin surface prior the light delivery.

The topical agent may be a precursor of photosensitizer.

According to other embodiments of the invention the fabric may comprise natural fibres, such as cotton, or a mix of natural fibres with manmade fibres.

According to an eighth aspect of the present invention there is provided a fabric comprising fibres coated with a dye which selectively reflects a therapeutic wavelength of electromagnetic radiation, such that one or more reflections from the dye contributes to transmission of said therapeutic wavelength of electromagnetic radiation through said fabric.

Preferably the dye substantially prevents absorption of said therapeutic wavelength by the fibres.

Preferably transmission of said therapeutic wavelength of electromagnetic radiation through said fabric is at least double the transmission of said wavelength through a similarly structured fabric comprising similar but undyed fibres.

According to a ninth aspect of the present invention there is provided a method for protection of the skin from electromagnetic radiation in sunlight that causes skin damage, comprising:

delivering some of the electromagnetic radiation from sunlight to the skin, through a material having the following optical properties:

absorption of at least a substantial proportion of the electromagnetic radiation in sunlight that causes skin damage; and transmission of a substantial amount of electromagnetic radiation in sunlight that has therapeutic effect for the human skin;

and thereby allowing exposure of the skin to electromagnetic radiation that has a therapeutic effect for human skin;

wherein the material is a fabric in accordance with the eighth aspect.

It will be appreciated that the optional or preferable features recited above will be applicable to various aspects of the invention.

It will be appreciated that the phrase "therapeutic effect for human skin" is to be construed broadly: for example radiation that destroys bacteria, but which has no significant other therapeutic or harmful effect on human skin should be considered to fall within the meaning of this phrase.

BRIEF DESCRIPTION OF THE DRAWINGS

Embodiments of the invention will hereafter be described, by way of example only, with reference to the accompanying drawings, in which.

DETAILED DESCRIPTION OF EMBODIMENTS

Figure 1:
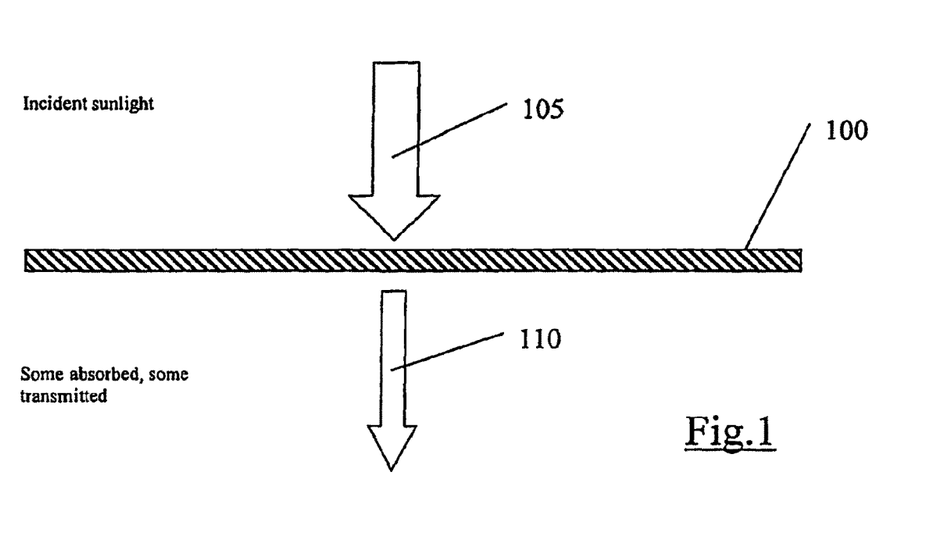
FIG. 1 is a schematic cross sectional view of a piece of material in accordance with an embodiment of the present invention, with incident and transmitted electromagnetic radiation illustrated schematically thereon.

With reference to FIG. 1, in one embodiment a material, designated 100, is shown schematically, with a larger arrow 105 illustrating full spectrum sunlight incident upon the material 100, and a smaller arrow 110 illustrating a lesser amount of radiation which has been transmitted through the material, the remainder having been effectively filtered by the material.

Importantly, certain wavelengths which exist in sunlight are known to be harmful to the skin. Generally, wavelengths in the ultraviolet part of the spectrum, about 100-400 nm, are considered harmful, and wavelengths between about 290 nm and 330 nm, where solar erythric response is maximal, are particularly dangerous. The optical properties of the material 100 are such that a substantial amount of the harmful radiation is filtered out. Certain wavelengths which exist in sunlight are known to have therapeutic effect: wavelengths of 400-500 nm, and in particular 400-420 nm, have been found to be therapeutic for acne and promote destruction of bacteria; wavelengths of 550-700 nm, preferably 590-670 nm (and in particular 590 nm and 632 nm) have been found to assist skin rejuvenation and wrinkle reduction, lead to improvement of blood circulation and stimulate hair growth range. Infrared light in the range of 700-900 nm been found to stimulate tissue healing; UVB light at around 380 nm has been found useful in the treatment of psoriasis and other conditions; and other wavelengths have been found therapeutic in hair removal, removal or reduction of excess pigmentation. The optical properties of the material 100 are such that a substantial amount of at least one type of therapeutic radiation is transmitted.

In one embodiment the material 100 is a fabric which transmits only a relatively small proportion of the incident sunlight 105, and transmits substantially only one or more parts of the spectrum which have a therapeutic effect. Such a fabric can be used for shirts, hats and other clothes. The material may transmit radiation in one or more spectral bands.

In one embodiment the fabric comprises a fabric which is made from a polymer such as polyester or nylon. or from a natural fabric, such, as cotton, or from a polymer/natural fabric combination. The fabric may optionally with a spandex (or elastane) component. The fabric fibres are coated with a die which scatters (or reflects) light of the spectral band which it is desired to transmit. Light of the desired spectral band can be transmitted through such a fabric by transmission through the fibres themselves (which may be somewhat transparent or translucent to the wavelengths of desired spectral band, depending on the fibre material and wavelength) and by multiple scattering from the dyed surfaces of the fibres. The latter mechanism is likely to be dominant, especially in the circumstances that the fibres are not very transparent or translucent to the wavelengths of desired spectral band. The construction of the fabric, being of fairly close weave, and the UV absorbing qualities of the fibre and dye, ensure that little or no harmful UV radiation is transmitted through the fabric to the wearer. An example of a dye suitable for use in a fabric used in clothing, such as for example a shirt or hat, for the treatment of acne (e.g. transmitting in the spectral band between 400 nm and 450 nm) is Pigments 105 SLO Period Blue, from the company Dharma Trading Co., which has good reflectivity in the blue part of the spectrum. Of course it will be appreciated that many other dyes, with good reflectivity in other parts of the spectrum, could be used to enhance transmission properties of a fabric in corresponding parts of the spectrum as desired.

Figure 2:
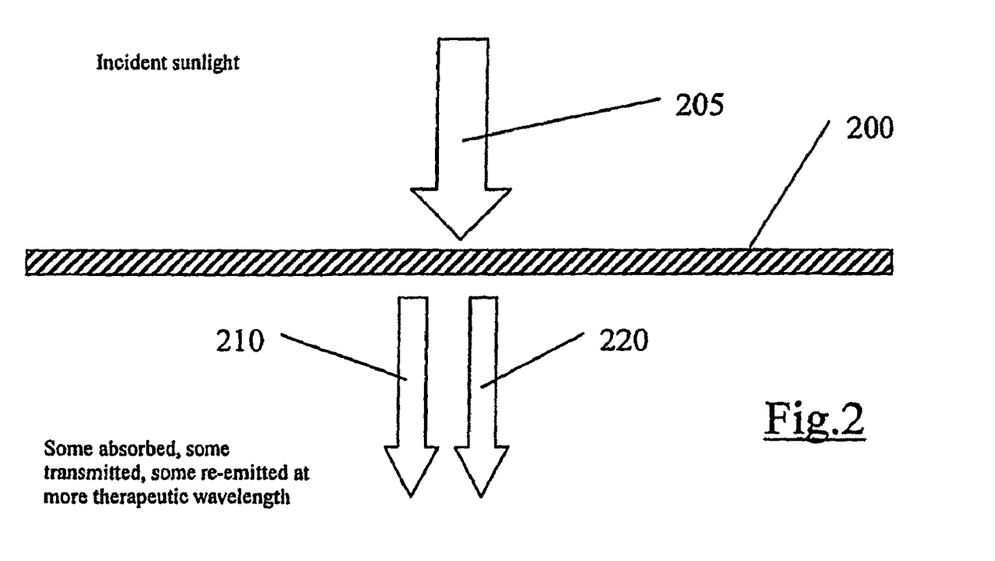
FIG. 2 is a schematic cross sectional view of a piece of material in accordance with an alternative embodiment of the present invention, with incident, emitted and transmitted electromagnetic radiation illustrated schematically thereon.

With reference to FIG. 2, in a second embodiment a material, designated 200, is shown schematically. In this embodiment some of the radiation of the incident sunlight is transmitted, some is absorbed by the material 200, and some of the absorbed radiation is re-emitted at one or more wavelengths which have a therapeutic effect. As illustrated in FIG. 2, a larger arrow 205 illustrates full spectrum sunlight incident upon the material 200, a first smaller arrow 210 illustrates a smaller amount of radiation which has been transmitted through the material 200 and a second smaller arrow 220 illustrates an amount of radiation which has been re-emitted by the material 200.

As with the first embodiment 100, the material 200 can be a fabric which can be used for shirts, hats and other clothes. The material 200 may transmit and/or emit radiation in one or more spectral bands.

It will be appreciated that a further (third) embodiment comprises a material in which substantially no sunlight is simply transmitted through the material, but in which some therapeutic radiation is emitted from the side of the material opposite to the side upon which the sunlight is incident. A schematic illustration of such an embodiment would effectively be the same as the illustration of FIG. 2, but with the first smaller arrow, 210, omitted. Such an embodiment will not, therefore, be explicitly illustrated in a separate drawing.

It will be appreciated that use of a material, such as is described in relation to the above general descriptions of three embodiments, to shield a subject from at least some of the harmful radiation in sunlight (or other electromagnetic radiation having a harmful component) so that therapeutic radiation is transmitted and/or emitted, so that it can reach a subject, can correspond to a method of protecting a subject from the harmful radiation, and a method of therapy. A particularly convenient form of such a method is to use clothing made from such a material, and to use sunlight as the light source. This allows hours of treatment to be undertaken conveniently, for example while walking outdoors, gardening or the like. In contrast many other methods of therapy using light require the patient to remain immobile adjacent the light source, sometimes for extended periods. Items of clothing that may be provided in accordance with embodiments of the invention will primarily include shirts and hats, and also include other clothing items such as (but not limited to) skirts and trousers. Of course, alternatives to clothing are possible: for example, a parasol or umbrella made from the material could provide a similar effect.

In one embodiment the optical properties of the material allow transmission and/or emission of wavelengths in the range 400-420 nm. Exposure of the skin of a subject to these wavelengths may provide a useful acne treatment. Radiation in this range of wavelengths interacts with porphyrin generated by bacteria, and this photodynamic reaction destroys the bacteria, reducing the acne. Such an embodiment does not preclude transmission and/or emission of a broader range of wavelengths, such as 400-440 nm or 400-490 nm, and some embodiments may target these wavelengths. In some embodiments other wavelengths which may be suitable for treatment of acne (and/or other conditions to be treated) can additionally or alternatively be targeted.

Light can interact with porphyrins produced by human cells. The effect can be amplified by applying topical cream with photosensitizing properties. Such a cream may include some precursors of porphyrins or other photosensitizing agents. Application of an appropriate substance, which in one embodiment can be a topical cream, may improve the efficacy of a method of skin treatment such as those described above. The method can include the use of one or more photosensitizing agents. In a variation, photosensitizing agents may be utilized in ways other than being applied to the skin: for example orally or intravenously administered photosensitizing agents could be used. Suitable topical creams and photosensitising agents are known per se and will not be describe herein.

Of course, wavelengths with therapeutic effect on conditions other than acne could be utilized. Wavelengths in the orange and red part of the visible spectrum are known to stimulate collagen growth and to have skin rejuvenation effect. Interaction of light in this spectral range with fibroblast stimulates its growth. Examples of some other uses phototherapy have been given above.

In preferred embodiments the material is a fabric, facilitating manufacture of comfortable clothing items from (or incorporating) such a material. In manufacture of a fabric having the desired optical properties, the following synthetics are examples of polymer materials which can conveniently be used: acetate; acrylic; nylon; latex; polyester; rayon. Of course, other materials could be used including natural fibres, such as cotton, or a mix of natural fibres with manmade fibres. It has been found particularly beneficial to use a fabric with a component of spandex, such as a nylon/spandex or poly-cotton/spandex fabric.

Fluorescent or filtering dye can be impregnated into a fibre or fabric. There is a large number of commercially available laser and fluorescent dyes which provide light emission in the visible and near infrared spectrum, and from which dyes suitable for emitting desired therapeutic wavelengths can be selected for use in a material. For example blue fluorescent dyes from COOMARIN group of dyes can be used to emit in the blue (400-440 nm) band. Similarly, commercially available fluorescent dyes which emit in other bands can be used as required. Typically, fabric can be dyed using standard methods. Dyes can be selected according to their optical characteristics, and it is desirable to select one or more dyes which minimise transmission of unwanted wavelengths such as UVA, UVB and UVC (unless those wavelengths are specifically required to treat conditions such as psoriasis). Use of dyes which are fluorescent in nature allows effective amplification of light at the specific wavelength, thus enhancing the desired therapeutic effect.

Tailored dyes, and in particular tailored fluorescent dyes, manufacture to reflect and emit at specific wavelengths are commercially available. Fluorescent dyes are available which emit in any desired 10-20 nm band (or a broader band if desired) from about 400 nm upwards. Some dyes are manufactured by the suppliers to allow transmission or amplification in the infrared spectrum, which can be useful in the treatment of certain conditions. Suitable dyes for creating a fabric which transmits and/or fluoresces in a desired spectral band are thus commercially available. The colour of the dye generally directly correlates to the wavelength of light that is desired to transmit through the garment, cloth, sunshade, polymer or synthetic material, film, umbrella etc. in order to treat specific conditions.

In one embodiment, in order to deliver therapeutic radiation to the skin of a subject while protecting the skin of the subject from harmful radiation the polymer-based fabric should:

be substantially, or at least partially, transparent (and/or translucent) to the desired therapeutic radiation;

absorb a substantial proportion of the harmful radiation part of sunlight; and convert at least some non-desired parts of the sunlight into the desired therapeutic radiation.

A nylon/spandex fabric dyed with a suitable fluorescent dye is one example of an effective embodiment. In some embodiments, concentration of the dye in the fabric should be high enough to absorb most of the harmful radiation (but see also the description below, of the embodiment of FIG. 4). By way of example, the following dyes can be used for transforming ultraviolet (UV) radiation into blue light: DAPI; Hoechst 33342. These dyes are known per se and sometimes used in fluorescent spectroscopy. Both absorb strongly between about 300 nm and 400 nm and emit (fluoresce) between about 400 nm and 500 nm.

Thus, for example, polyester or nylon spandex fabric impregnated with DAPI dye can be used to protect the skin from UV radiation and enhance delivery of blue light in the range 400 nm-450 nm and should therefore provide therapeutic effect for acne.

The fluorescent dye known as Cy3 dye, has an excitation spectrum in the range of 470-570 nm and a fluorescence (emission) spectrum in the red spectrum 550-650 nm. Broadly speaking this dye may be considered to 'shift' the wavelength of incident radiation from a shorter wavelength to a longer wavelength. This dye can be imbedded into a polymer for manufacture of a fabric that can be used to protect a user from the harmful wavelengths in sunlight while allowing exposure (of an area covered by the fabric) to wavelengths which stimulate fibroblast.

For example, a synthetic fabric, such as that sold under the trademark CoolDry, could be manufactured in a form dyed with Cy3 dye to deliver to the skin red radiation. It will be appreciated that in this example, at least some radiation in the range of 470-570 nm is absorbed and converted to radiation in the range of 550-650 nm which has the desired therapeutic effect. Thus in this embodiment at least part of the absorbed radiation utilized for *conversion' to therapeutic radiation is not considered particularly harmful.

In some embodiments a combination of a several dyes can be used to provide better protection from harmful radiation, and/or to provide exposure of the skin of the subject to more, or a greater range of, therapeutic radiation. For example, use of both DAPI and Cy3 dyes to create a fabric would provide to the skin blue light in the range 400-440 nm (effectively converted from incident UV by the DAPI) useful for acne treatment and also red light in the range 550-650 nm (effectively converted from light in the 470-570 nm range by the Cy3) useful for skin regeneration.

Figure 3A:
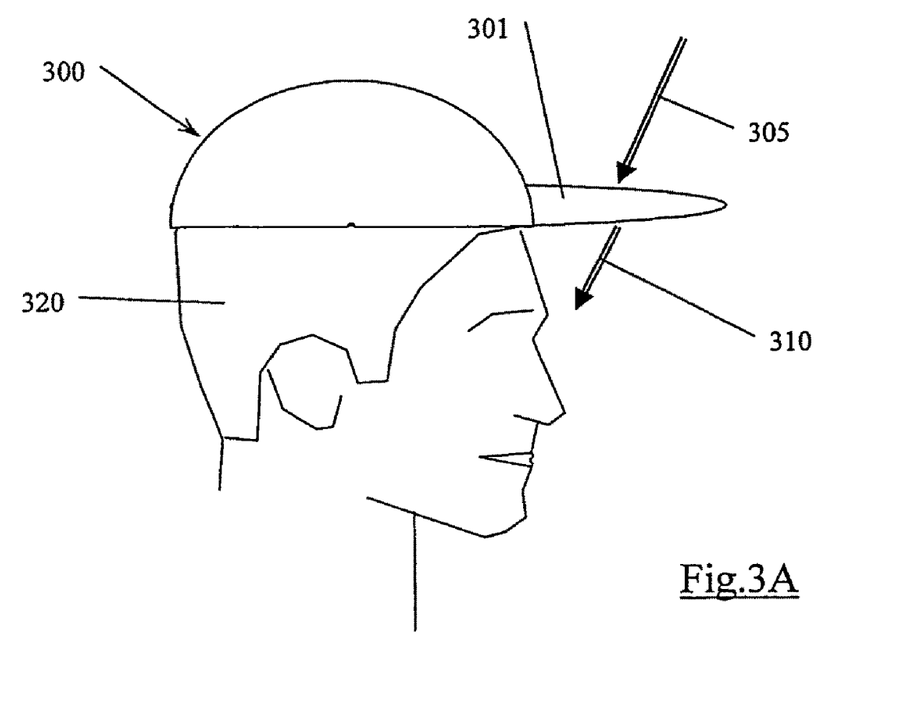
FIG. 3A is a schematic illustration of an item of clothing, in the form of a baseball cap, in accordance with an embodiment of the present invention, in use.

With reference to FIG. 3A, an embodiment of an item of clothing in the form of hat, illustrated as a baseball cap 300, has a brim 301 formed from a material in accordance with the embodiment of FIG. 2 (that is, by the second embodiment, although it will be appreciated that variations could be provided by use of the first or third of the three embodiments described above). Sunlight, illustrated by arrow 305, incident upon the brim 301, has a substantial amount of the harmful radiation filtered from it, and by a combination of transmission and re-emission results in radiation 310, which includes a substantial therapeutic component (and a reduced harmful component compared to sunlight) being incident upon the face of a wearer 320 of the baseball cap 300. Although a baseball cap 300 is illustrated the invention is, of course, applicable to other forms of headwear and perhaps most appropriately to a hat with a continuous broad brim. In a variation the entire hat, with or without a brim, may be formed from a material adapted to protect the head of the wearer from harmful components of sunlight but to expose the head of the wearer to increased levels of wavelengths believed to stimulate hair growth, in the 550-700 nm yellow-red range. This may facilitate a convenient treatment for undesired baldness or thinning hair.

Figure 3B:
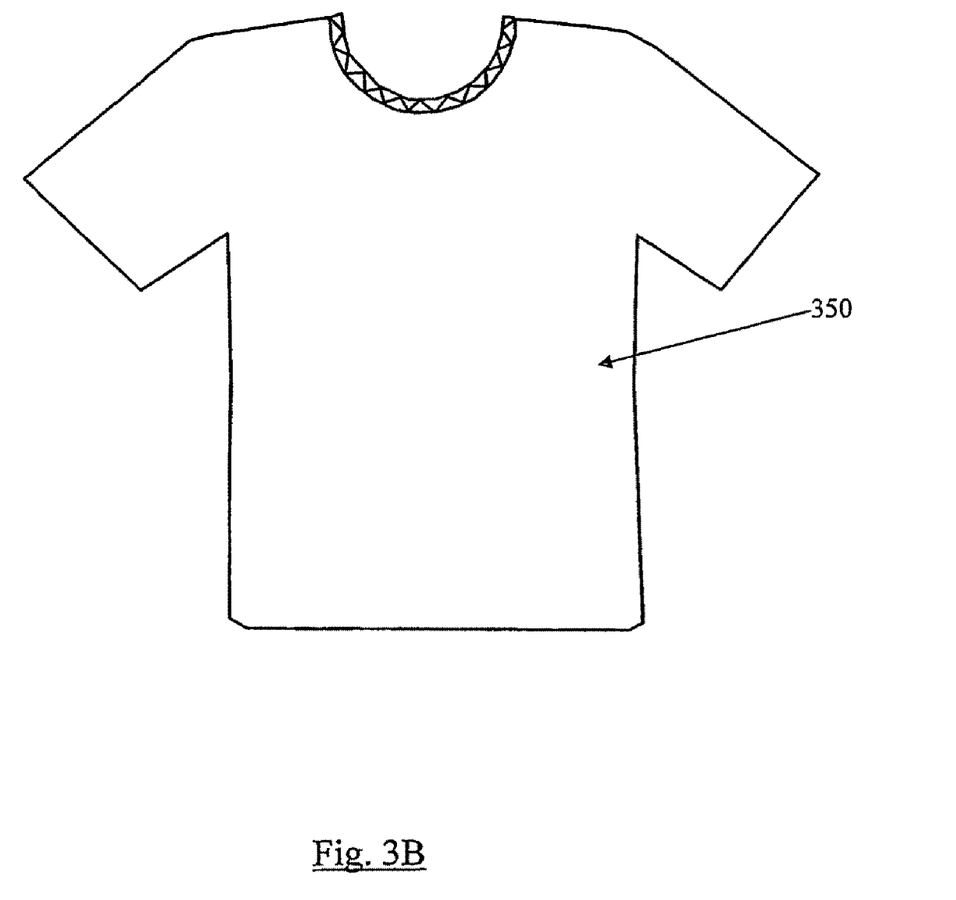
FIG. 3B is a schematic illustration of an item of clothing, in the form of a shirt, in accordance with an embodiment of the present invention.

One currently preferred embodiment, shown schematically in FIG. 3B, is a shirt 350 which is suitable for use in protecting a wearer from harmful components of sunlight while treating acne. The shirt 350 is, in this embodiment, formed from a nylon/spandex fabric with 84% nylon and 16% spandex and a weight of approximately 170 grams per square meter ($^{58}/_{60}$"×240 g/y). The fabric has a weave density of about 95%, and preferably of 97% or more (and is specified as 70D/48F nylon and 4OD spandex). Such a fabric is able to provide effective UV protection. The shirt fabric is dyed with a fluorescent dye, and in one embodiment the dye ADS129BE, (poly (9,9-dioctylfluorenyl-2,7-diyl) end capped with dimethylphenyl) available from American Dye Source Inc, is used. This dye absorbs in the UV and has a photoluminescent maximum at 438 nm, emitting from about 410 nm upwards. Other related dyes (such as ADS229BE, ADS329BE, ADS429BE, ADS131 BE, ADS231 BE, ADS331 BE, ADS431 BE), which typically have photoluminescent maximum at slightly lower wavelengths may also be appropriate for use. It will be appreciated that wearing of such a shirt in sunlight will offer protection from the harmful UV in sunlight while allowing significant exposure to wavelengths in the blue spectral band that has been found to be therapeutic for acne. In preferred embodiments, due to the fluorescent emission at the target wavelengths, the provided intensity of radiation in the desired therapeutic spectral band may exceed that in natural sunlight. Although a short sleeved shirt 30 is illustrated the invention is, of course, applicable to other styles of shirt and perhaps most appropriately to a shirt with long sleeves to provide better protection from the harmful effects of sunlight. The description of this embodiment is, of course given by way of illustration only, and it will be appreciated that various related embodiments, incorporating different fibres and/or dyes, and for treating different conditions with different wavelengths could be provided.

It will be appreciated that there are a number of possible ways of applying a dye to a fabric in order to make embodiments of the invention. Possibly the most straightforward is to dye the entire fabric, for example by immersion in a liquid dye, resulting in all surfaces of the fabric fibers being covered with dye (preferably fluorescent dye). One alternative is to use polymer fibres with imbedded dye. This method is more expensive because it requires specialist manufacturing methods. A further option is to apply, for example by spraying, fluorescent dye onto one surface of the fabric. An advantage of this method is that fluorescent dye may be applied only to the inner surface of the fabric forming an item of clothing, so that from outside the item of clothing the fabric does not appear to conspicuously fluoresce. In this case the fabric must be designed or selected so that adequate intensity of radiation in the excitation spectral band of the dye penetrates the fabric and reaches the die.

Figure 4:
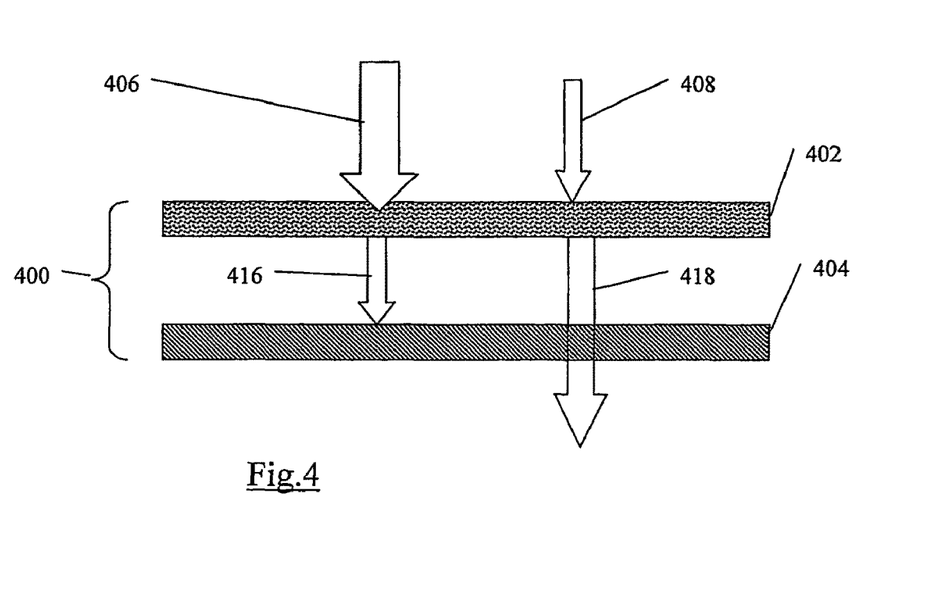
FIG. 4 is a schematic cross sectional exploded view of a piece of material in accordance with an alternative embodiment of the present invention, with incident, emitted and transmitted radiation illustrated schematically thereon.

Additionally, or alternatively, a material in accordance with the present invention, may comprise more than one layer, with different layers having different optical properties, but so that the material as a whole has the desired optical properties. For example, as illustrated in FIG. 4 in schematic, exploded form, a material generally designated 400, has a first, florescent, layer 402 and a second, filtration, layer 404. The first, fluorescent, layer 402, includes a dye which absorbs harmful radiation and emits therapeutic radiation. The second, filtration, layer 404 is substantially transparent to the therapeutic radiation but substantially opaque to harmful radiation. FIG. 4 illustrates schematically a situation where a considerable amount of incident harmful radiation 406 and a relatively small amount of incident therapeutic radiation 408 are incident upon the first layer 402. The first, fluorescent, layer 402 absorbs a certain amount of harmful radiation and both transmits and emits therapeutic radiation, so that a reduced amount of harmful radiation 416 and an enhanced amount of therapeutic radiation 418 reach the second, filtration, layer 404. The second, filtration, layer 404 filters out the remaining harmful radiation, so that substantially no harmful radiation passes through the material 400, but so that substantially all of the enhanced amount of therapeutic radiation 418 exits the material. It will be appreciated that FIG. 4 is an exploded view and that in practical embodiments the layers 402, 404 would usually be in contact with each other. It should also be appreciated that the representation of the radiation is schematic, and that the incident harmful and therapeutic radiation would be likely to be components of the spectrum of sunlight. In one embodiment the second, filtration, layer 404 can be a coating applied to a first, fluorescent layer 402 which is in the form of a fabric. The coating could comprise nano particles of inorganic substance such as a suitable metal oxide, such as zinc oxide, which have been found to be effective in filtering ultra-violet radiation while allowing transmission of visible light.

Figure 5A:
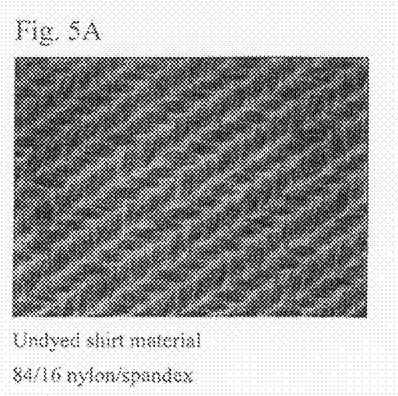
FIGS. 5A and 5B are, respectively, images of an undyed material and a dyed material suitable for manufacturing an embodiment of the invention in the form of a shirt.
Figure 5B:
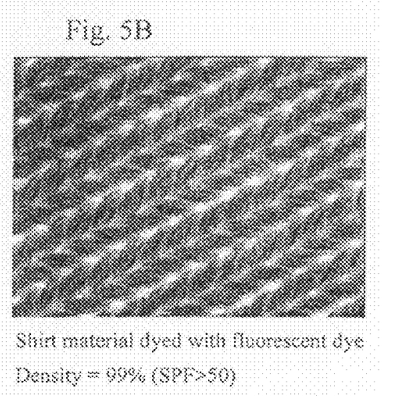

FIGS. 5A and 5B illustrate an undyed material (griege) and a dyed material suitable for use in manufacturing the shirt described above with reference to FIG. 3B.

Figure 6A:
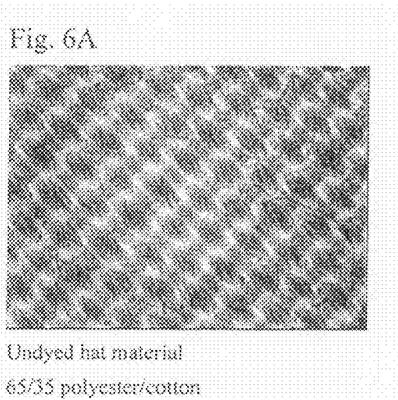
FIGS. 6A and 6B are, respectively, images of an undyed material and a dyed material suitable for manufacturing an embodiment of the invention in the form of a hat.
Figure 6B:
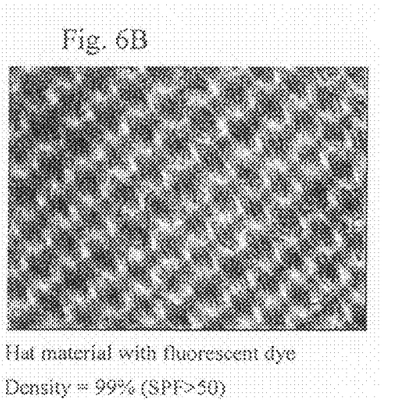

FIGS. 6A and 6B illustrate an undyed material and a dyed material suitable for manufacture of a hat.

Figure 5C:
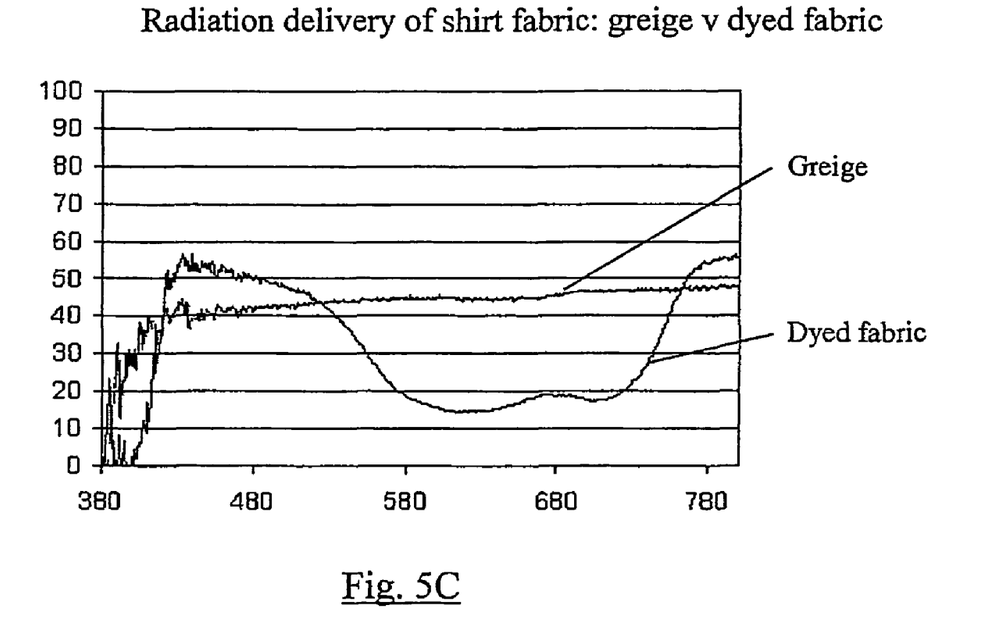
FIG. 5C illustrates radiation delivery of the material of FIG. 5B.

FIG. 5B illustrates an 84% nylon 16% spandex material described above with reference to FIG. 3B dyed with fluorescent dye ADS129BE. FIG. 5C illustrates radiation delivery when exposed to sunlight of the dyed material and, for comparison, of the same fabric but without the dye. As illustrated in FIG. 5C the dyed material delivers an increased (by about 30%) amount of radiation in the spectral band between 400 nm and 500 nm (therapeutic for acne treatment) and a reduced amount of radiation in nearby spectral bands.

Compared to either sunlight or delivery through greige the amount of ultraviolet (below 400 nm) radiation is substantially reduced. The material delivers wavelengths between 400 nm and 500 nm more than twice (and almost three times) as effectively as it delivers wavelengths between about 580 nm and 700 nm. It will be noted that delivery of wavelengths above about 760 nm is also enhanced. This is due to the dye being an effective reflector of these wavelengths, enhancing transmission of these wavelengths through the fabric by multiple scattering of the dyed fibre surfaces and reducing absorption by the fibres. This may provide an additional benefit since infrared radiation at such wavelengths may have therapeutic properties.

It will be appreciated that suitable selection from one of many commercially available fluorescent dyes will allow selection of a spectral band in which radiation delivery can be increased in order to provide a therapeutic effect.

It is to be understood that/if any prior art publication is referred to herein, such reference does not constitute an admission that the publication forms a part of the common general knowledge in the art, in Australia or in any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

Variations and modifications can be made in respect of the invention described above and defined in the following statement of claim.

The invention claimed is:

1. A protective material comprising a fabric having the following optical properties:
    absorption of at least a portion of the electromagnetic radiation in sunlight that causes skin damage;
    and
    conversion of at least part of the absorbed radiation to a converted radiation having a therapeutic effect on human skin, said converted radiation having wavelengths of 400 to 490 nm, wavelengths of 590 to 670 nm or wavelengths of 700 to 900 nm.

2. The material of claim 1 wherein said optical properties are at least partially caused by said fabric having been dyed by at least one pigment.

3. The material of claim 2 wherein said fabric is made from polymer.

4. The material of claim 3 wherein said radiation that has a therapeutic effect on human skin includes wavelengths absorbed by porphyrin.

5. The material of claim 4 wherein said radiation that has a therapeutic effect on human skin includes wavelengths in the range of 400 to 490 nm.

6. The material of claim 3 wherein said radiation that has a therapeutic effect on human skin includes wavelengths which stimulate collagen growth.

7. The material of claim 6 wherein said radiation that has a therapeutic effect on human skin includes wavelengths in the range of 590 to 670 nm.

8. The material of claim 4 wherein said radiation that has a therapeutic effect on human skin includes wavelengths which stimulate collagen growth.

9. The material of claim 8 wherein said radiation that has a therapeutic effect on human skin includes wavelengths in the range of 400 to 490 nm and in the range of 590 to 670 nm.

10. The material of claim 3 wherein said radiation that has a therapeutic effect on human skin includes wavelengths that stimulate tissue healing and being in the range of 700 to 900 nm.

11. The material of claim 4 wherein said radiation that has a therapeutic effect on human skin includes wavelengths that stimulate tissue healing and being in the range of 700 to 900 nm.

12. The material of claim 6 wherein said radiation that has a therapeutic effect on human skin includes wavelengths that stimulate tissue healing and being in the range of 700 to 900 nm.

13. The material of claim 8 wherein said radiation that has a therapeutic effect on human skin includes wavelengths that stimulate tissue healing and being in the range of 700 to 900 nm.

14. The material of claim 5 wherein at least some of the electromagnetic radiation in sunlight that causes skin damage and which is absorbed by the fabric is ultra-violet radiation.

15. A portable item which includes at least a portion made from a material having optical properties which, in use, can protect at least an area of the wearer's skin from electromagnetic radiation in sunlight that causes skin damage, while allowing radiation that has a therapeutic effect on human skin to be transmitted from said material to said area of the wearer's skin, wherein the optical properties include:
   absorption of at least a portion of the electromagnetic radiation in sunlight that causes skin damage; and
   conversion of at least part of the absorbed radiation to a converted radiation having a therapeutic effect on human skin, said converted radiation having wavelengths of 400 to 490 nm, wavelengths of 590 to 670 nm or wavelengths of 700 to 900 nm.

16. A method for protection of human skin from electromagnetic radiation in sunlight that causes skin damage and for therapeutic treatment of human skin, comprising covering the human skin with a material having the following optical properties:
   absorption of at least a portion of the electromagnetic radiation in sunlight that causes skin damage; and
   conversion of at least part of the absorbed radiation to converted radiation having a therapeutic effect on human skin, said converted radiation having wavelengths of 400 to 490 nm, wavelengths of 590 to 670 nm or wavelengths of 700 to 900 nm.

17. The method of claim 16 wherein the optical properties of the material further comprises:
   transmission of electromagnetic radiation in sunlight that has a therapeutic effect on human skin.

18. The method of claim 16 wherein the material is a fabric dyed by at least one fluorescent pigment.

19. The method of claim 16 wherein the converted radiation includes wavelengths in the range of 400 to 490 nm that are absorbed by porphyrin.

20. The method of claim 16 wherein the converted radiation includes wavelengths in the range of 590 to 670 nm that stimulate collagen growth.

21. The method of claim 16 wherein said converted radiation includes wavelengths in the range of 700 to 900 nm that stimulate tissue healing.

22. The method of claim 16 wherein the material is made from a polymer such as acetate; acrylic; nylon; latex; polyester; rayon.

23. The method of claim 16 wherein the material is made from a natural fiber, such as cotton, or from a polymer/natural fiber combination.

24. The method of claim 22 or 23 wherein the material further comprises a component of spandex, such as a nylon/spandex or polycotton/spandex combination.

25. The method of claim 18 wherein said at least one pigment is selected among fluorescent dyes from the coomarin group, DAPI; Hoechst 33342, Cy3, Cy5, ADS129BE, ADS229BE, ADS329BE, ADS429BE, ADS131BE, ADS231 BE, ADS331BE and ADS431BE.

26. The method of claim 16 wherein the material is formed into a portable item selected from an umbrella, a parasol, a sunshade or an item of clothing.

27. The material of claim 1 wherein the optical properties of the material further comprises:
   transmission of electromagnetic radiation in sunlight that has a therapeutic effect on human skin.

28. The material of claim 1 wherein the material is made from a polymer such as acetate; acrylic; nylon; latex; polyester; rayon.

29. The material of claim 1 wherein the material is made from a natural fiber, such as cotton, or from a polymer/natural fiber combination.

30. The material of claim 28 or 29 wherein the material further comprises a component of spandex, such as a nylon/spandex or polycotton/spandex combination.

31. The material of claim 2 wherein said at least one pigment is selected among fluorescent dyes from the coomarin group, DAPI; Hoechst 33342, Cy3, Cy5, ADS129BE, ADS229BE, ADS329BE, ADS429BE, ADS131BE, ADS231BE, ADS331BE and ADS431BE.

32. The material of claim 1 wherein the material is formed into a portable item selected from an umbrella, a parasol, a sunshade or an item of clothing.

33. The item of claim 15 wherein the optical properties of the material further comprises:
   transmission of electromagnetic radiation in sunlight that has a therapeutic effect on human skin.

34. The item of claim 15 wherein the material is made from a polymer such as acetate; acrylic; nylon; latex; polyester; rayon.

35. The item of claim 15 wherein the material is made from a natural fiber, such as cotton, or from a polymer/natural fiber combination.

36. The item of claim 34 or 35 wherein the material further comprises a component of spandex, such as a nylon/spandex or polycotton/spandex combination.

37. The item of claim 15 wherein said material is dyed with at least one pigment selected among fluorescent dyes from the coomarin group, DAPI; Hoechst 33342, Cy3, Cy5, ADS129BE, ADS229BE, ADS329BE, ADS429BE, ADS131BE, ADS231BE, ADS331BE and ADS431BE.

38. The item of claim 37 wherein the material is formed into an umbrella, a parasol, a sunshade or an item of clothing.

* * * * *